(12) United States Patent
Rolla (10) Patent No.: US 8,216,193 B2
(45) Date of Patent: Jul. 10, 2012

(54) SYRINGE FOR ADMINISTERING MULTIPLE DOSES COMPRISING AN INJECTION NEEDLE WITH STERILITY PROTECTION

(75) Inventor: Jose Santiago Rolla, Buenos Aires (AR)

(73) Assignee: Jose S. Rolla, Buenos Aires (AR)

( * ) Notice: Subject to any disclaimer, the term of this patent is extended or adjusted under 35 U.S.C. 154(b) by 476 days.

(21) Appl. No.: 11/913,431

(22) PCT Filed: Mar. 2, 2006

(86) PCT No.: PCT/ES2006/070025
§ 371 (c)(1),
(2), (4) Date: Jun. 27, 2008

(87) PCT Pub. No.: WO2007/042592
PCT Pub. Date: Apr. 19, 2007

(65) Prior Publication Data
US 2008/0281274 A1 Nov. 13, 2008

(30) Foreign Application Priority Data

May 2, 2005 (AR) .............................. P20050101742
Nov. 30, 2005 (AR) .............................. P20050105002

(51) Int. Cl.
*A61M 5/00* (2006.01)
*A61M 5/24* (2006.01)
*A61M 5/28* (2006.01)
*A61M 5/315* (2006.01)

(52) U.S. Cl. ........ 604/208; 604/200; 604/207; 604/210; 604/218; 604/244

(58) Field of Classification Search ................... 604/110, 604/111, 181, 187, 199, 200, 201, 207, 208, 604/210, 218, 220, 227, 228, 239, 240, 242, 243, 244, 246, 93.01
See application file for complete search history.

(56) References Cited

U.S. PATENT DOCUMENTS

| 2,373,520 | A | * | 4/1945 | Wallin | 604/210 |
| 2,502,639 | A | * | 4/1950 | Blake | 604/210 |
| 2,764,981 | A | | 2/1956 | Helmer et al. | |
| 2,869,541 | A | * | 1/1959 | Helmer et al. | 604/210 |
| 3,126,004 | A | | 3/1964 | Sarnoff | 604/111 |
| 3,934,586 | A | * | 1/1976 | Easton et al. | 604/208 |
| 4,366,912 | A | * | 1/1983 | Matukura et al. | 215/247 |
| 4,367,738 | A | * | 1/1983 | Legendre et al. | 604/110 |
| 4,444,335 | A | * | 4/1984 | Wood et al. | 222/43 |

(Continued)

FOREIGN PATENT DOCUMENTS
DE    4134911    4/1993

(Continued)

*Primary Examiner* — Kevin C Sirmons
*Assistant Examiner* — Shefali Patel
(74) *Attorney, Agent, or Firm* — Oliff & Berridge, PLC (57) ABSTRACT

A plurality of dosage-control members are detachably connected to the plunger rod of a multi-dose syringe along two opposing sides of the rod. Each dosage-control member has a cut in which the external diameter of the top rim of the syringe fits to prevent forward and reverse movement of the rod. Removal of one dosage-control member from one of the two opposing sides of the rod permits forward movement of the rod and plunger until the top rim snaps into the cut of another dosage-control member. Flexible salient arms extend obliquely from the rod in one-to-one correspondence with the dosage-control members to prevent reverse movement of the rod.

15 Claims, 7 Drawing Sheets

U.S. PATENT DOCUMENTS

| | | | | |
|---|---|---|---|---|
| 4,826,483 A | * | 5/1989 | Molnar, IV | 604/110 |
| 4,995,869 A | * | 2/1991 | McCarthy | 604/110 |
| 5,250,030 A | * | 10/1993 | Corsich | 604/110 |
| 5,318,544 A | | 6/1994 | Drypen et al. | 604/210 |
| 5,476,106 A | * | 12/1995 | Gartz | 128/898 |
| 5,556,384 A | * | 9/1996 | da Encarnac ao | 604/110 |
| 5,975,355 A | * | 11/1999 | Cecala et al. | 222/43 |
| 6,013,056 A | * | 1/2000 | Pettersen | 604/110 |
| 6,530,903 B2 | * | 3/2003 | Wang et al. | 604/195 |
| 6,533,756 B2 | * | 3/2003 | Schoenfeld et al. | 604/110 |
| 6,786,891 B2 | * | 9/2004 | Hiejima | 604/164.01 |
| 2004/0015120 A1 | * | 1/2004 | Berman et al. | 604/11 |
| 2005/0137532 A1 | | 6/2005 | Rolla | |

FOREIGN PATENT DOCUMENTS

GB     1230522     5/1971

\* cited by examiner

SYRINGE FOR ADMINISTERING MULTIPLE DOSES COMPRISING AN INJECTION NEEDLE WITH STERILITY PROTECTION

This application is a national stage application of International Application No. PCT/ES2006/070025, filed Mar. 2, 2006, which claims priority to Argentina Patent Application No. P20050101742, filed May 2, 2005 and Argentina Patent Application No. P20050105002, filed on Nov. 30, 2005.

This invention has an application in the medicine as well as veterinary medicine fields in general, for the injection of medicaments subcutaneously, mainly vaccines and insulin, and in a massive way for the application of the injectable substances in an optimum way by transferring them into the bottles of solutions of intravenous use or injecting them by means of their tubes perforating the elastomer seals or to be connected to different devices and ways of application of doses of injectable medicine substances or administered orally.

PRIOR TECHNIQUE

Several devices are known for the application of injectable medicaments up to the present time, most of them require the decanting of the content of the ampoules that contain them into the syringes to be injected directly into the patient or into the interior of systems of intravenous injection. Among the total amount of injectable medication, very few syringes contain the medication, being of larger world use the ones used for the application of vaccines that habitually contain only one dose or the ones that contain several doses of insulin, that are generally used individually by each patient, what makes the use of complementary devices necessary.

Scarce medicaments for other uses are bottled in the syringes with which they shall be injected, and almost none of them contain multiple doses due to the inconvenience of maintaining their sterility in successive injections. The syringes of a widespread use in the world are the disposable ones used to inject medicaments directly into the patient, and in a massive way in the world, in which it is necessary to decant the injectable medicament when it is directly into the patient or in most of the cases to transfer it into bottles of intravenous use for their application in a programmed personal way.

The syringes that have multiple doses shall have means that allow their accurate dosage and guarantee its sterility. In order to allow multiple dosages there are various kinds of syringes with means to obtain that, as in the case, among others, of the syringes disclosed by the documents GB 786,931, U.S. Pat. No. 4,246,898, U.S. Pat. No. 4,642,102, WO 99/07421 and U.S. Pat. No. 6,562,007.

Most of these systems of screwing of dosage tops that do not offer enough safety guarantees, mainly in the cases that the injection is applied by the patient himself/herself.

SUMMARY OF THE INVENTION

The present invention refers to a syringe to administer multiple doses of medicament, with great exactitude by means of dosage tops that detach from the rod that permits the solution to the problems of the previous technique. One particular characteristic of the invention is the fact that the plunger is freely located inside the syringe but fixed by an annular rim to the command end of the syringe by means of a laminar precinct that encircles the rim of the lug of the syringe. The plunger that is immobilized provides inviolability guarantees of the syringe and allows a better connection with the propelling rod that is achieved by rotary movements that are made with the rod. It is important that this connection should be perfect to guarantee the exact dosage of each injection and the safe of the syringe. Once the connections is made, when continuing the rotary movement, the peripheral tear takes place in annular discontinued areas of the annular rim of the plunger, what causes its release for its impelling function. This invention also foresees improvements to immobilize the rod, preventing backward movements by means of fine tie salient arms that are detached in an oblique angle from the body of the rod. Moreover, it incorporates another complementary system to block the rod by means of cuts of the interior rim of the dosage tops that embed and tie in the annular rim of the lug. These systems of immobilization of the rod can act separately or in a cooperative way, with the main aim of avoiding, whit its immobilization, the entrance of external ambient air that would produce its contamination. This invention incorporates the use of bevelled double-pointed needles, protected from the contact with ambient contaminators by means of plastic transparent impermeable bubbles that cover them, thermoformed as a means to avoid its contamination, protecting the sterility of the injecting systems by preventing the contact of the protected needle and the medicament with the non sterile ambient air, or the contact with any other contaminated element, that is impossible to guarantee with the use of the one-pointed conventional needles, which make essential the opening of the end of the syringe for the connection of a new needle when injecting each dose.

OBJECTS AND ADVANTAGES OF THE INVENTION

To the specified ends, the syringe to administer multiple doses, aimed at the administration of two or more doses of a substance contained inside it, comprises:
 a cylindrical tube in one of whose ends there is an opening whereas in the opposite end there is an injection opening, inside said tube, closing the opening, there is an impelling plunger apt to move in a longitudinal way; and
 a rod, with a command end and a lover end to be connected to the impelling plunger, said rod has a transversal section, preferably cross-shaped, of a smaller size than the interior diameter of the tube;
Where said rod comprises a plurality of dosage tops that act as detachable members by means of respective structural weakening of the rod, such dosage tops detach from the body of said rod exceeding the interior diameter of the tube:
where the said dosage tops act the opening of the tube, preventing the forward movement of the rod and the entrance of the impelling plunger in the tube, in a magnitude corresponding to a medicinal dose;
said syringe is characterized in that:
several top means are foreseen in the opening that are useful to determine an area of reduced interior diameter in relation to the interior diameter of the tube, but larger than the transversal section of the rod and the impelling plunger, an area of external rim with a diameter that exceeds the external diameter of the tube, or both cases;
means of clocking are foreseen in the rod cooperate with the above mentioned top means, preventing the backward movement of said rod inside the tube;
an extreme elastomer seal is foreseen to close the injection opening permanently and it is adapted to be perforated by means of a sharp element; and a device of a disposable hypodermic needle is foreseen to couple by means of one if its ends in the injection opening. Said device has a needle to perforate the extreme elastomer seal and communicate with the interior of the tube and it is adapted to provide an injection needle on its opposite side.

According to the invention, it is advantageous that the syringe have its two closed by hermetic elastomer seals that allow successive multiple injections using in each of them, needles with bevelled points protected by wrappings that guarantee their original sterility, such security is not possible with the use of conventional needles of one point, which it is necessary to expose the needle to the ambient air to carry out its connection, and that act alters sterility. Similar contamination takes place with the ampoule bottles that contain multiple doses, in which it is necessary to inject air so the injectable substance is aspirated by the rise of its inner pressure.

Another advantage of the invention consists of the great economic saving it represents, since for each dose that is injected, the dangerous transference of the injectable substance is avoided and the cost of an ampoule and a disposable syringe is saved, which is of an indispensable use with the present technology. Besides, for its minimum volume in comparison with the same content with the conventional systems, the storage and transport costs are also considerably lowered.

This syringe that contains multiple doses, is ideal to inject and dose injectable substances in a massive way, or inject them into bottles of solutions of intravenous use, without being in contact with the ambient air, or to be injected directly into the tubes of intravenous use by means of the perforation with the needle of the elastomer membranes that they with this aim.

They are also useful for the injection of medicaments and electrolytes used in renal dialysis and for the application of subcutaneous injections in a massive way, mainly during campaigns of vaccination, insulin, allergy medicaments, homeopathic medicaments and for any other kind of medicament of a subcutaneous application.

In the case of the application of insulin, as the doses vary according to the needs of the patient, this system is apt to contain partial conventional doses, in such a way that removing the necessary amount of dosage tops, the patient himself completes the necessary dose, in each application.

It can also be used to administer medicaments in a fast and safe way orally, mainly in hydration plans and provision of electrolytes in pediatric or elderly patients.

It is an advantage of this configuration that the patient can dose the exact dose blindly, only by means of the touch of the dosage tops.

It is also advantageous the implementation of systems the immobilize the elastomer plunger that blocks the command end, which has an annular rim that fixes it to the syringe lug, by means of a rigid laminar precinct that prevents its rotary movement, acting as an indicator of inviolability and allowing the perfect connection of the plunger to any fitting system by means of rotation with the lower end of the rod.

Another advantage consists in the moment when the laminar precinct that fixes the rim of the plunger, has a central circular sector, whose upper embossed surface adjacent to its rim, acts as a top for the blocking salient arms that the rod has in its rims.

In one of its best manufacture variants, the annular rim of the plunger has an discontinued annular groove, that is interrupted by sectors that connect its rims, and are equidistantly separated with areas of smaller thickness in the interior rim where its tear and release take place when the connection and fitting of the rod is finished, when the rotary movements continues.

Another advantage stems from the implementation of a systems for the immobilization of the rod after the injection of each dose, that guarantees the impossible alteration of the following dose or the adulteration of its content and above all, when preventing its backward movement the entrance of contaminated ambient air into the syringe is also avoided, which, apart from its seriousness, would alter the accuracy of the dose.

Another advantage consists in the fact that the configuration of the dosage tops can be generally done in the same way, as a consequence all the doses shall be same.

Another advantage is that in some specific cases, according to special needs, the dosage tops are different to determine the injection of progressively increasing doses.

Another advantage consists in the implementation of the protection wrapping for both ends of bevelled double-pointed needle, with impermeable wrappings of thermoplastic material, that are easily perforated, guaranteeing the penetration of the injectable substance in the organism with the same sterility level with it was bottled.

BRIEF DESCRIPTION OF THE DRAWINGS

For the sake of clarity and to understand the object of the invention, it is illustrated in different figures, in which it has been represented in one of the preferred embodiments, which is purely exemplary and therefore non-limiting.

DESCRIPTION OF THE PREFERRED MANUFACTURE VARIANTS

As it is shown in the figures, it is possible to see that the syringe consists of a cylindrical tube 1 with an opening end 2 and injection end 3, an impelling plunger 4 apt to move longitudinally and a rod 5 with a command end 50 and a lower end 51 that can be connected to the impelling plunger.

The rod 5, of a preferred transversal cruciform section, comprises a plurality of dosage tops 6 that act as detachable members, through the respective structural weakening 61, that detach from the body of said rod exceeding the interior diameter of the tube. Said dosage tops are apt to act against the opening 2 of the tube, preventing the forward movement of said rod and the motion of the impelling plunger inside the tube in an amount corresponding to a medicinal dose indicated with D.

In order to avoid the backward movement of the rod 5 once the injection operation has started, some dosage tops 7 are foreseen and they are arranged as a piece with an external rim that encircles the opening 2 of the tube 1 and cooperate with the blocking means 60 foreseen as cuts 60 formed in the internal rim of the dosage tops 6.

According to a variant in the invention, the means of top are arranged as an inferior rim that encircles the opening 2 of the tube 1, that cooperate with the blocking means 8 arranged as narrow salient arms adjacent to the lower rim of each of the dosage tops 6 of the rod 5 and that extend in an oblique way towards the end of the command end 50 in a diameter that is larger than the one inside the tube 1.

According to the invention, in order to close the injection end permanently, there is a seal 9 made of elastomer that is adapted to be perforated by a sharp element.

In addition, there is a device that consists of a hypodermic needle 10 to be coupled through one of its ends in the injection opening. By means of this needle device, arranged as a double needle as it shall be explained hereinafter in more detail, on the one hand it is possible to perforate the seal and communicate with the interior of the tube and on the other hand, it provides an injection needle on its opposite end.

As it is shown in FIGS. 12-15, the dosage tops planned as detachable members 6 extend along their free end in an extension 63, those extensions shall be straight or curved, so that they can identify detachable members of different sizes; apart from the sense of the extension it can also be used to distinguish or differentiate the detachable members.

The dosage tops 6, apart from the connection with the rod 5 through the respective structural weakening 61, are adjacent to each other, through other structural weakening 62.

Figure 2:
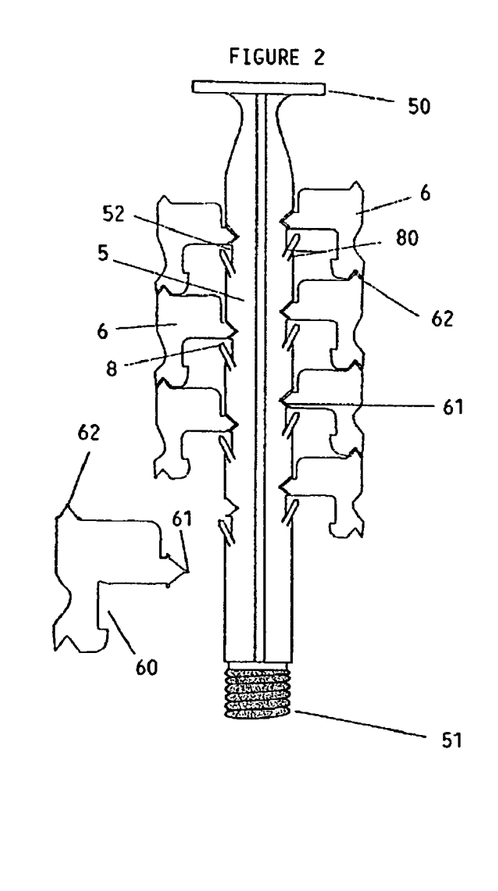
FIG. 2 is a view in elevation of a preferred embodiment of the rod where it is possible to see the detachable members or dosage tops.

Complying to the invention, the dosage tops 6 shall only be placed in one rim of the rod 5 or, as an alternative, over at least two rims that are diametrically opposed to the longitudinal portion of the rod 5, but carried longitudinally, the ones on one side in comparison to the ones on the other side, as it is more clearly shown in FIG. 2.

Besides, and as it is shown in the figure the dosage tops 6 comprise visual and/or tactile identification means 64, including relief, cutting, etc. . . .

Figure 3:
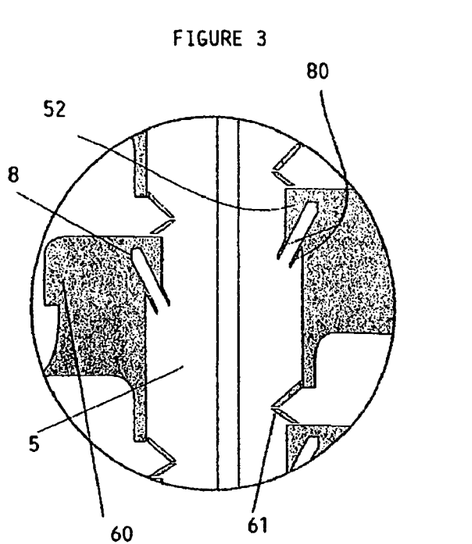
FIG. 3 shows, in detail, a longitudinal part of the rod showing a preferred manufacture variant of the blocking salient arms.
Figure 4:
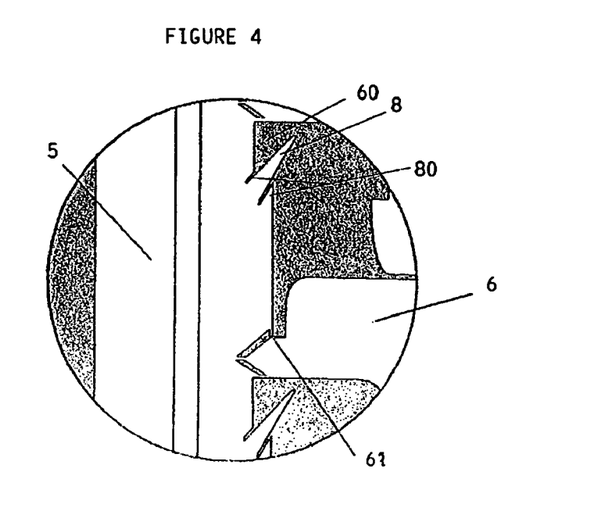
FIG. 4, in a similar way to FIG. 3, shows a detail of one part of the rod with another manufacture variant of the blocking salient arms.
Figure 5:
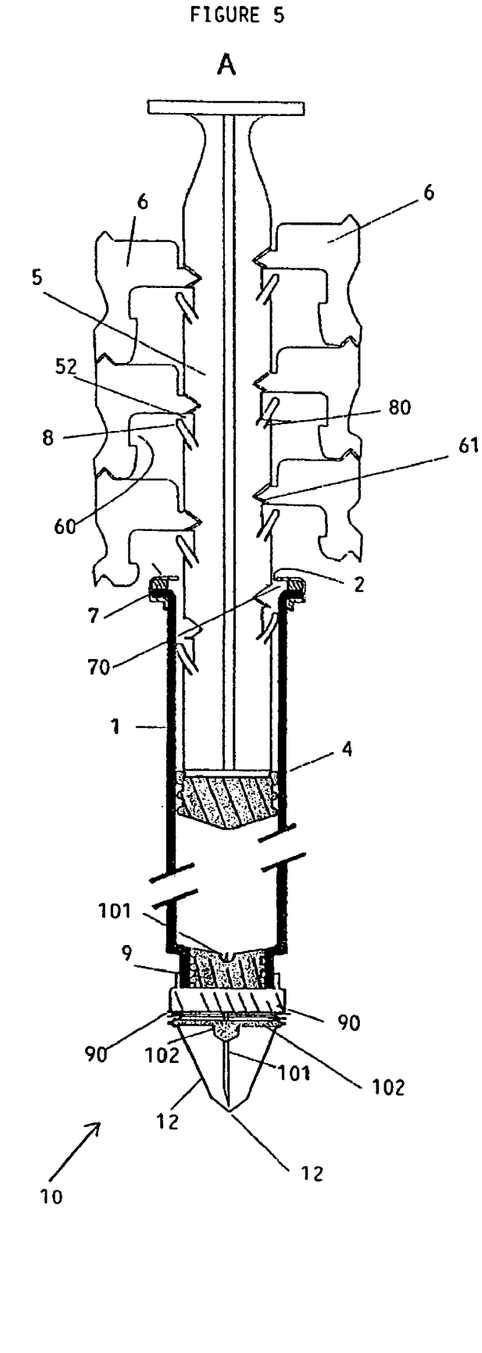
FIG. 5 is an analogous view to FIGS. 1A and 1B to show the penetration of the rod inside the tube and the folding of the blocking salient arms in the interior area.
Figure 6:
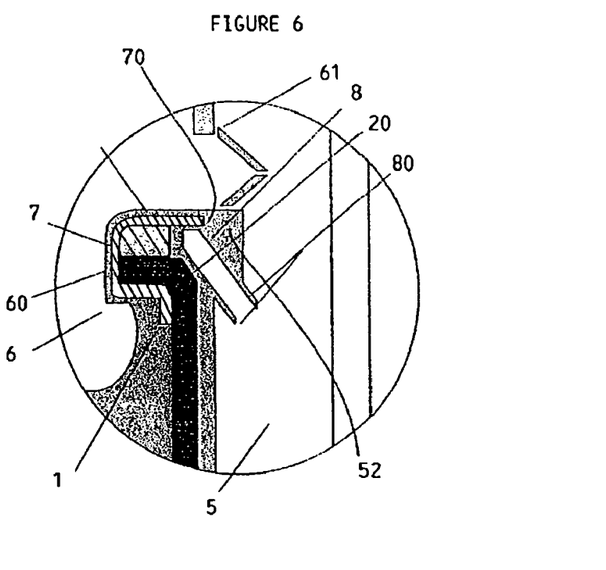
FIG. 6 is a detailed view of the insertion area of the rod in the opening of the tube, showing the function of the blocking salient arms.

As it can clearly be seen in FIGS. 3 and 4, in order to favour the folding and bending of the salient arms 8, there are grooves 80 that continue the direction of the upper and lower rims, extending to the inside of the rod 5. In addition, it can be seen that the salient arms 8 are either straight or in a sharp shape.

As it can be seen in FIGS. 3 and 4, in accordance with a preferred variant of the invention, in the rim of the rod 5 there are cuts 52 that hold the respective salient arms 8 when bending when they are introduced inside the tubular body 1 of the syringe with the forward movement of the rod 5.

Figure 7:
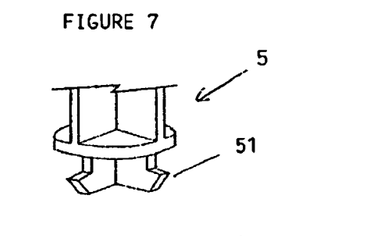
FIG. 7 is a view in perspective that shows a detail of the coupling of the injection end of the rod over one manufacture variant of the impelling plunger.
Figure 8:
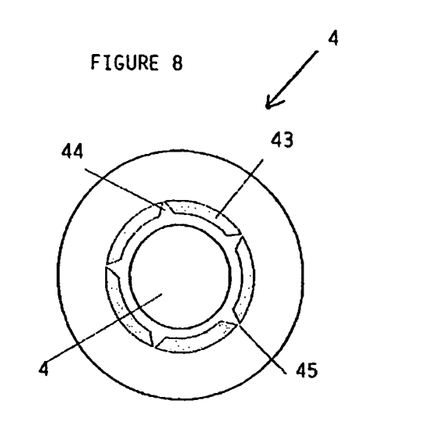
FIGS. 8, 9A-9B show respective views in an upper plan, lateral elevation and transversal section of another preferred configuration of the impelling plunger.
Figure 9A:
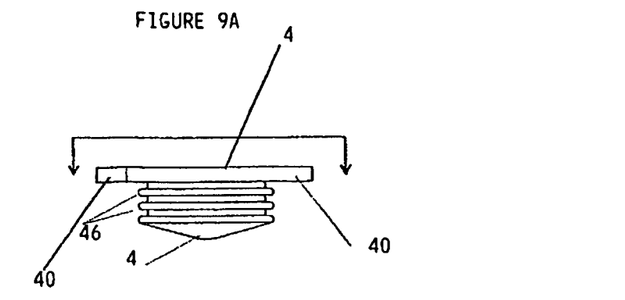
Figure 9B:
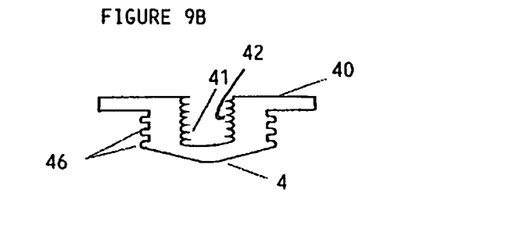
Figure 10A:
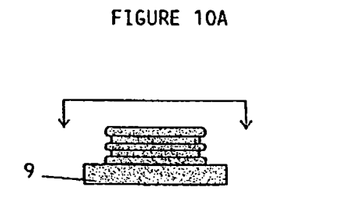
FIGS. 10A-10B show respective views in a lateral elevation and transversal section of the sealing top of the injection end of the syringe.
Figure 10B:
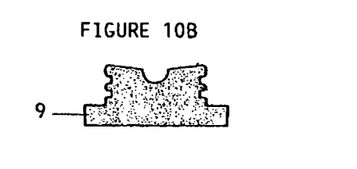

As it can be seen in FIGS. 7 to 9 the impelling plunger 4 is planned as a cylindrical top with an annular rim 40 in its upper end and with a central cavity 41 comprising some means 42 to connect the injection end 51 of the rod 5, for instance through turning movements, in a hook shape as it is shown in FIG. 7 as well as in a screw shape as it is shown in FIG. 9B. Apart form that, in accordance with a preferred variant, the plunger 4 is fixed to the tube 1 by means of a precinct 11, whose central part is breakable, that extends around the opening (2).

Alternatively the plunger 4 is formed by an annular rim 40 that has the same diameter as the largest diameter of the opening 2, with a discontinued annular groove 43, interrupted regularly by a plurality of segments 44 that go through it, in a radial sense connecting both rims, the ends that are connected to the inner rim are wider than connected to the external rim, that finish in an angular shape 45, determining weakened areas of rupture in response to forced rotary movements. In this way, when the rupture of the segments 44 takes place through the weakened parts through the turn of the rod 5, the annular rim 40 is dissociated from the plunger and becomes attached to the opening to from the blocking means, through its external part to act with the dosage tops as well as for its internal part to act in cooperation with the salient arms.

For this configuration of the plunger 4 and to allow the blocking arms to top, it is necessary that the segment of the tubular body of the syringe that is adjacent to the interior rim of the opening 2 have a bevel 20.

Figure 1A:
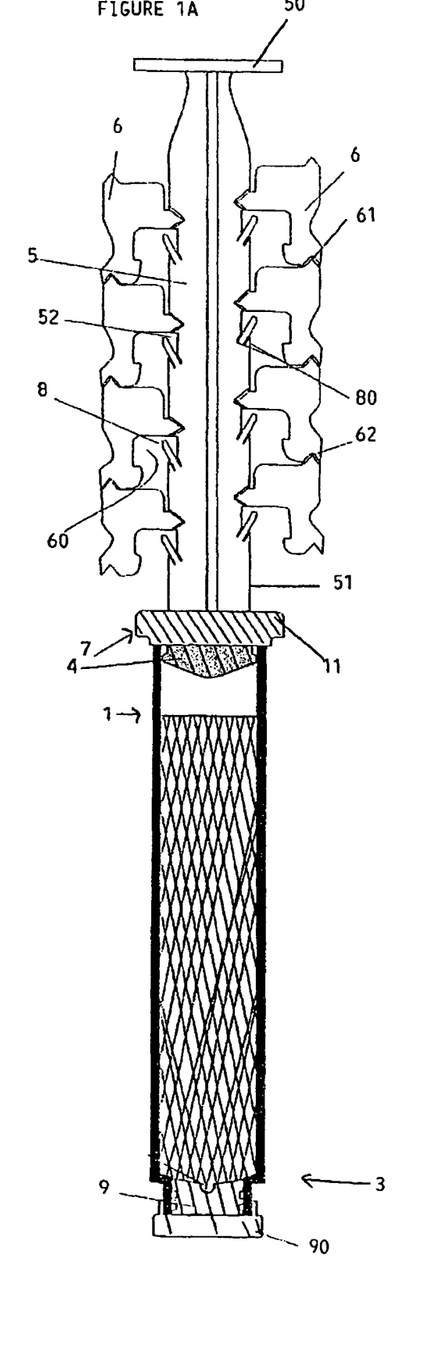
FIG. 1A shows a syringe in accordance with the invention partially longitudinally sectioned with the rod that is united to the impelling plunger.
Figure 11:
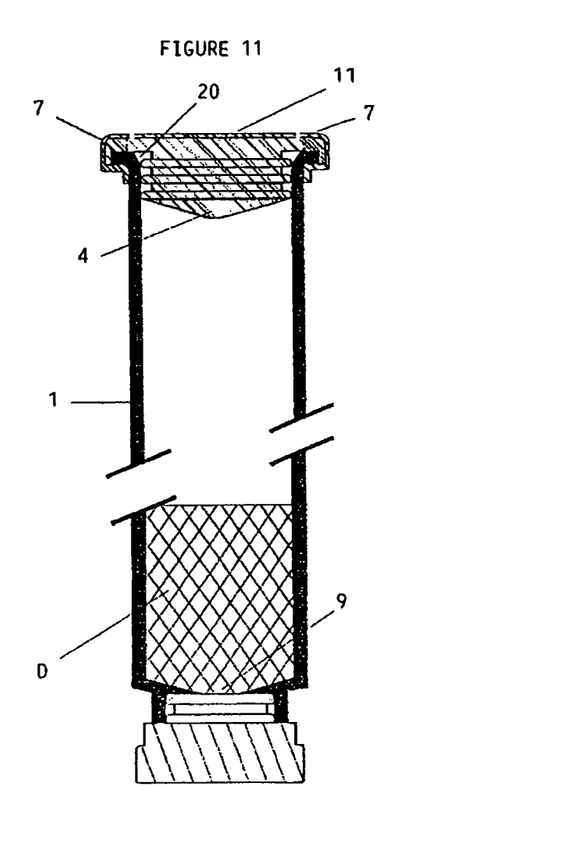
FIG. 11 shows the tube of the syringe partially sectioned, without the command rod, with the impelling plunger sealed closing its opening and the sealing top of the injection end, forming a hermetic path a medicine solution
Figure 12A:
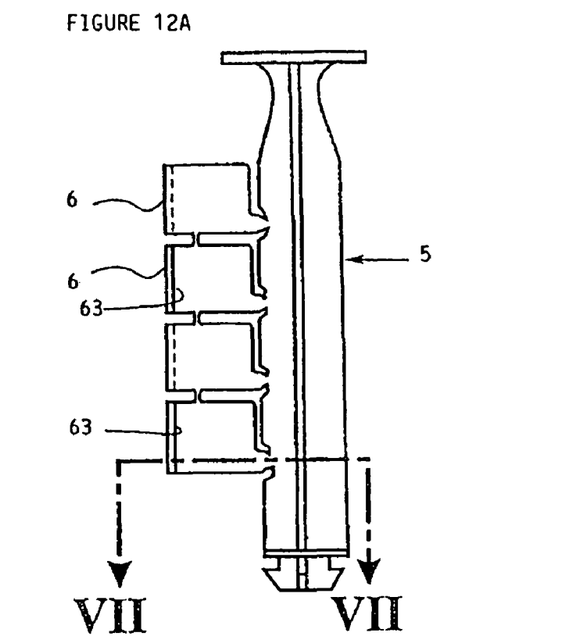
FIGS. 12A-12B and 13A-13B show respective views in a lateral elevation and lower plant of manufacture variants of the rod and dosage tops.
Figure 12B:
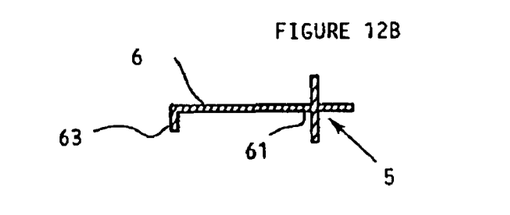
Figure 13A:
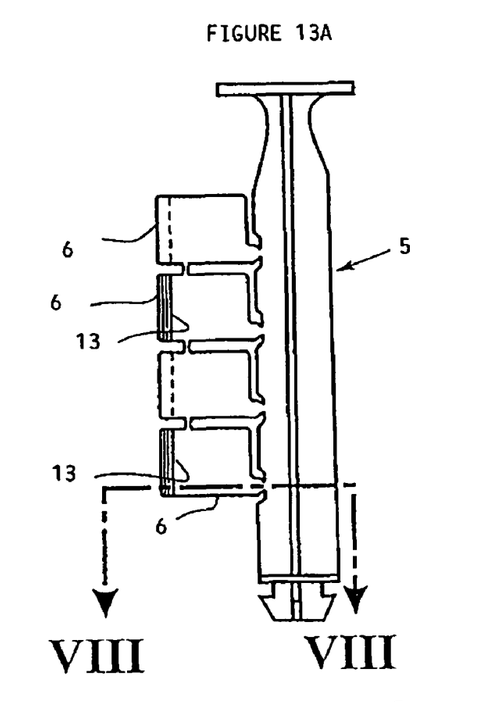
Figure 13B:
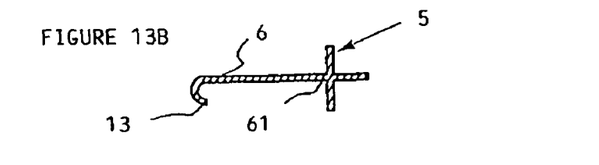
Figure 14:
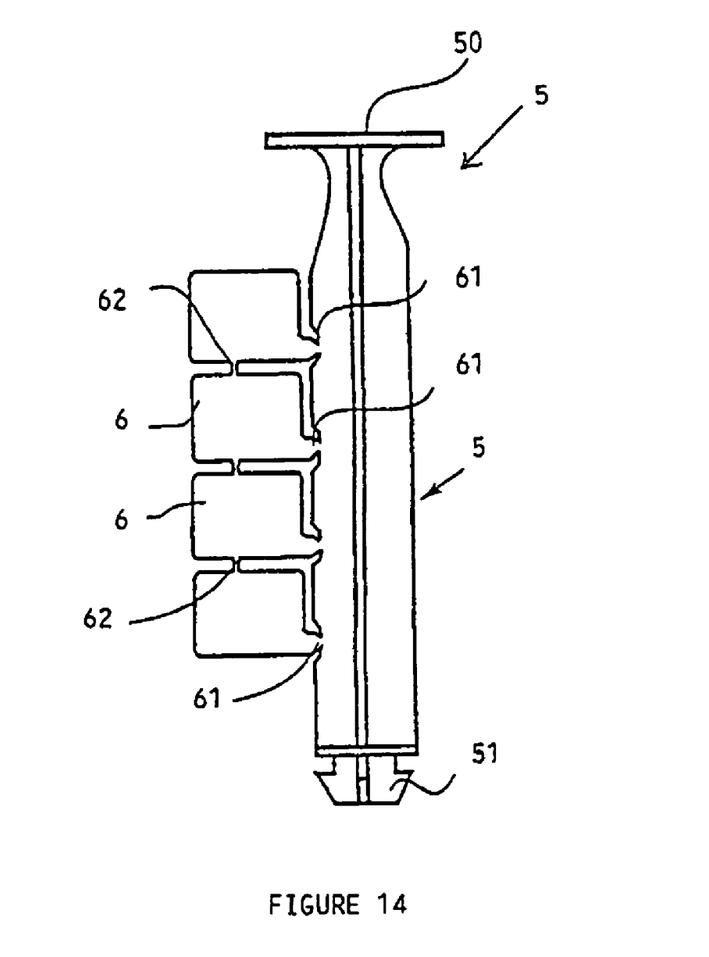
FIGS. 14 and 15 show views in elevation of other alternative configurations of the injection rod.
Figure 15:
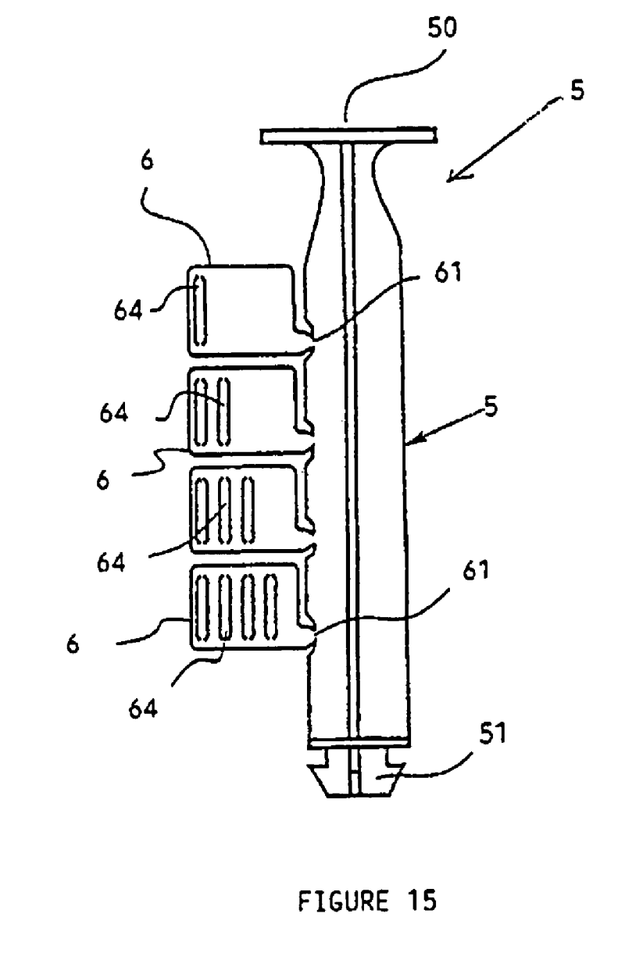
Figure 16:
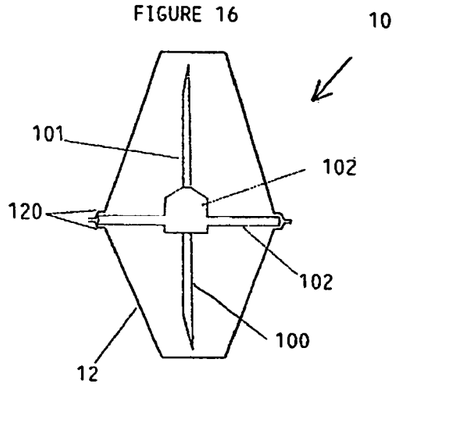
FIGS. 16 to 22 show different details of the needle device with a protective wrapping in the different configurations.
Figure 17:
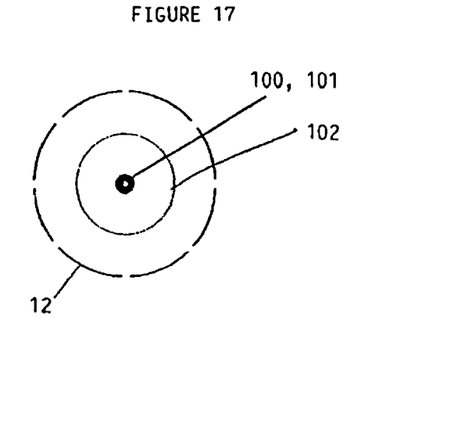
Figure 18:
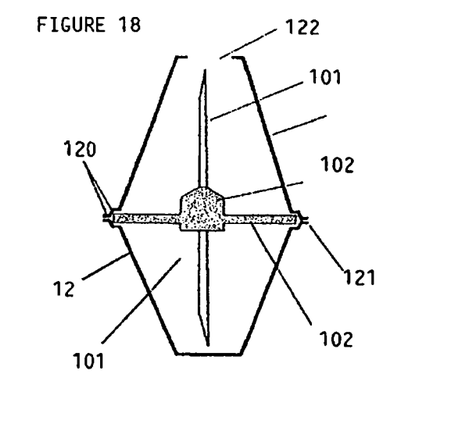
Figure 19:
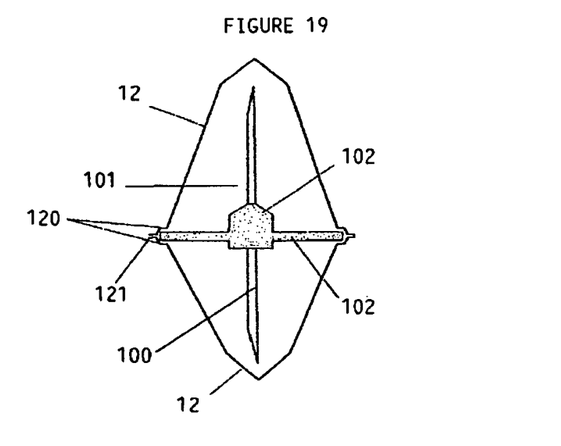
Figure 20:
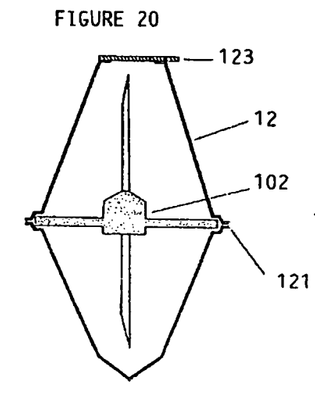
Figure 21:
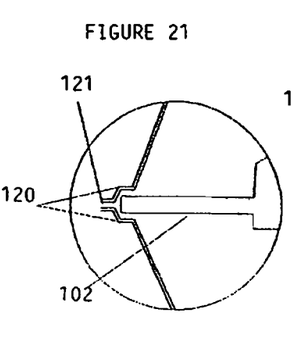
Figure 22:
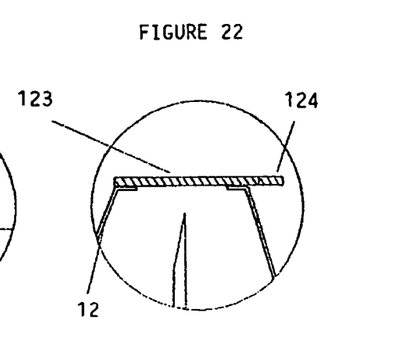

As it can be seen in FIG. 1A, the permanent elastomer top 9, is coupled in the injection opening 3 and can be additionally fixed by means of a laminar precinct 90 apt to be perforated with a sharp element. According to it, and as it is shown in FIG. 11, the tube 1, without the rod 5, can act as an injection link with its opening 2 closed by the impelling plunger 4 and the injection end 3 by means of the top 9. After that, the rod 5, can be connected to the plunger 4 by means of the above mentioned turning movement providing a needle ready to be used as it was herein previously explained.

In reference to FIGS. 16 to 22, it can be seen that the needle device 10 consists of two portions of needle 100, 101 that are arranged in a line and with injections points opposed to each other that are placed over a transversal support 102. In accordance with the invention, there is a protection wrapping 12 with the shape of a bubble made of thermoplastic material, preferably transparent and apt to be perforated by the corresponding portions of needle 100, 101.

According to a preferred manufacture variant, the protection wrapping 12 consists of its frustum-conic opposite ends that join in the area of the largest diameter by means of the union of their rims 120, as the level of a transversal support 102, with narrow unsealed sectors 121, aimed at releasing the gases contained in said protection wrapping.

It may be useful that the parts that form the protection wrapping 12 have, in the inner part of their largest diameter, a circular cavity 120 aimed at receiving the transversal support 102 of the needle device 10. Apart from that, in a preferred configuration, the ends of the frustum-conic portions of the protection wrapping 12, are finished in a flat surface.

It may be advisable for the ends of the frustum-conic portions of the protection wrapping 12 to have a conic finish 121 that extends from a transversal segment of a circular section 120.

The ends protection wrapping 12 may also have a central perforation 122 with a perimeter annular rim. Here, this central perforation 122 with a perimeter annular rim. Here, this central perforation 122 can be closed by means of a material of different physical characteristics 123, that is attached to the perimeter rim, sectors 124 that project from the perimeter of the protection wrapping 12.

Functioning as a Whole

Figure 1B:
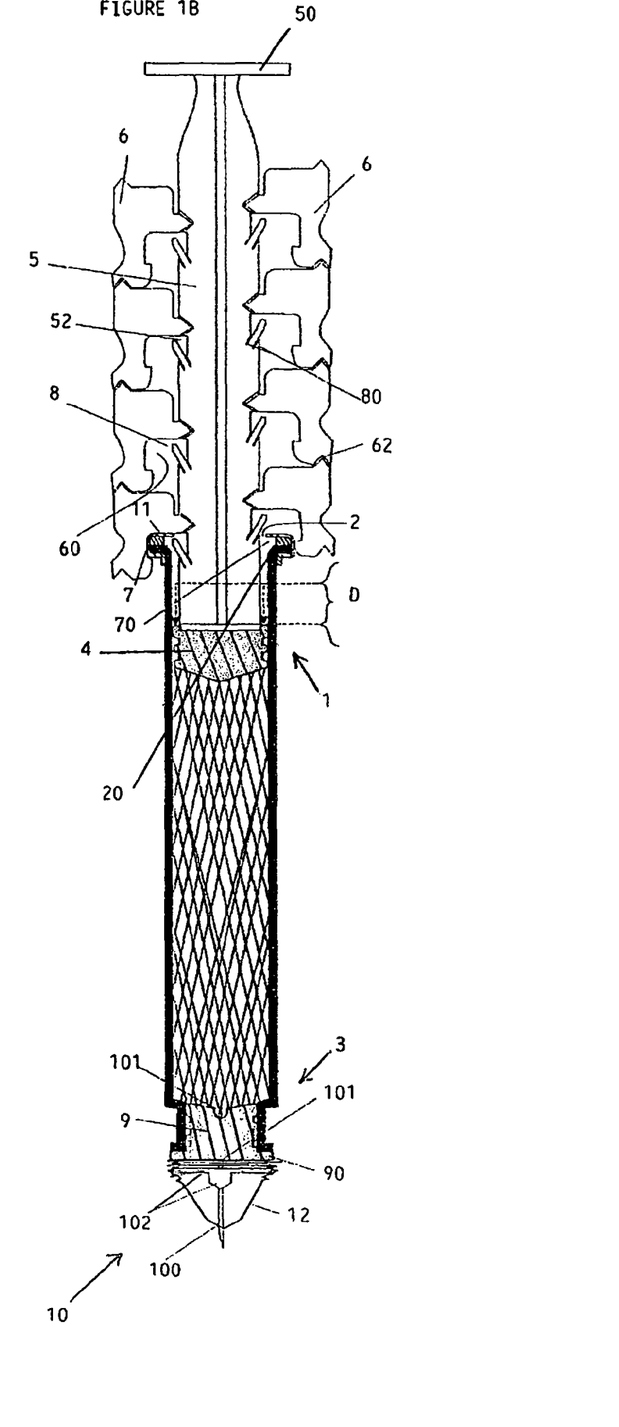
FIG. 1B is an analogous view to FIG. 1 but after removing the interior gases by injection to the outside through the needle.

As it is shown in FIG. 1A, the impelling plunger 4 is joined to the rod 5, closing the opening 2 of the tube in such a way that said plunger can advance inside the tube until one of the dosage tops 6 meets the top 7 of the opening of the tube, as it is shown in FIG. 1B. Once this position is reached, even when the rod 5 is still being pushed it shall not be able to advance, besides, said rod cannot move backwards either because the cut 60 of the dosage top fits in the top 7 until said dosage top 6 is removed through its breakable section 61.

Once said first dosage top 6 is removed from the rod 5, it is able to advance inside the tube 1 and obtain the forward movement of the impelling plunger 4 along part of its path corresponding to the separation in regard to the nearest dosage top 6 adjacent longitudinally. The path covered by the plunger 4 shall correspond to a dose of medicinal substance D expelled through the injection opening 3. The proceeding is repeated from here, except when the first salient arm 8 is already introduced in the tube, in such a way that an additional blocking takes place, which prevents the backward movement of the rod 5 as well.

When the present invention is put into practice, modifications may undoubtedly be introduced as regards details in the manufacture and shape, without moving away from the main principles that are clearly substantiated in the claims hereinafter.

The invention claimed is:

1. A syringe for administering multiple medicinal doses, the syringe comprising:
   a cylindrical tube having a first end, an opposing second end, a circular interior diameter, and a circular exterior diameter;
   a top rim connected to and encircling the first end of the tube, the top rim having a circular interior diameter that is smaller than the circular interior diameter of the tube, a circular exterior diameter that is greater than the circular exterior diameter of the tube, and an interior groove;
   a plunger disposed within the tube for medicinal dosing by forward movement of the plunger toward the second end of the tube;
   a rod having a command end, an opposing injection end releasably engaging the plunger, and a cruciform transversal section that is smaller than the interior diameter of the tube;
   a plurality of dosage-control members detachably connected to the rod by breakable structural weakenings spaced along two opposing sides of the rod, each dosage-control member having a cut in which the exterior diameter of the top rim fits to prevent forward and reverse movement of the rod when the top rim is received by the cut, such that removal of one dosage-control member from one of the two opposing sides of the rod permits forward movement of the rod and plunger until the top rim snaps into the cut of another dosage-control member detachably connected to the other of the two opposing sides of the rod;
   a plurality of flexible salient arms extending obliquely from the rod toward the command end in one-to-one correspondence with the dosage-control members, each salient arm extending into the interior groove of the top rim to prevent reverse movement of the rod when the top rim snaps into the cut of the corresponding dosage-control member;
   an elastomer seal attached to the second end of the tube; and
   a double-ended needle device having a first end for perforating the elastomer seal and an opposing second end for administering medicinal doses.

2. A syringe according to claim 1, wherein the dosage-control members are detachably connected to the rod as two columns of dosage-control members on opposing sides of the rod, and wherein the two columns are longitudinally shifted with respect to each other.

3. The syringe according to claim 1, wherein said salient arms have grooves that continue in the direction of either of the two opposing at sides of the rod extending towards the rod.

4. The syringe according to claim 1, wherein the two opposite sides of the rod have cuts that hold respective salient arms when bending said salient arms when the salient arms are introduced inside the tube with the forward movement of the rod.

5. A syringe according to claim 1, wherein the first end of the tube has a beveled opening.

6. The syringe according to claim 1, wherein the plunger is shaped as a cylindrical top with an annular rim and a central portion with a central cavity with connection means to be connected to the injection end of the rod, and said plunger is fixed in the tube by means of a breakable precinct with an embossed area in the center.

7. The syringe according to claim 6, wherein said annular rim has at least the same diameter as the interior diameter of the tube and a discontinued annular groove, interrupted regularly by a plurality of segments that go through the discontinued annular groove in a radial direction connecting said annular rim to the central portion, where ends of the segments connected to the central portion are wider than the angle ends joined to an edge of the interior groove and defines weakened areas of rupture in response to forced rotary movements of the rod.

8. The syringe according to claim 1, wherein the elastomer seal is fixed by means of a laminar precinct configured to be perforated with a sharp element.

9. The syringe according to claim 1, wherein the needle device consists of:
   two portions of a needle aligned and having opposite injection points that are mounted over a transversal support and that define the first end and second end; and
   a protection wrapping with the shape of a bubble made of thermoplastic, transparent material configured to be perforated by the corresponding portions of the needle.

10. The syringe according to claim 9, wherein the protection wrapping has frustum-conic opposite ends and is arranged such that the frustum-conic opposite ends are joined in an area of a largest diameter by means of a union of their rims at a level of the transversal support, such union of the rims having gas-permeable areas to release any gases contained in said protection wrapping.

11. The syringe according to claim 10, wherein both ends that make up the protection wrapping have, in an inside of their largest diameter a circular cavity where the transversal support of the needle device is fixed.

12. The syringe according to claim 11, wherein the frustum-conic ends of the protection wrapping finish in a flat surface.

13. The syringe according to claim 11, wherein the frustum-conic ends of the protection wrapping finish in a conic shape, from a transversal segment with a circular section.

14. The syringe according to claim 11, wherein at least one of the ends of the protection wrapping has a central perforation, with a perimeter annular rim.

15. The syringe according to claim 14, wherein said central perforation is closed by impermeable material that is attached to the perimeter rim, with sectors that prolong from a perimeter of the protection wrapping.

* * * * *